(12) United States Patent
Fujimoto et al.

(10) Patent No.: US 9,012,873 B2
(45) Date of Patent: Apr. 21, 2015

(54) TREATMENT PLANNING SYSTEM, DEVICE FOR CALCULATING A SCANNING PATH AND PARTICLE THERAPY SYSTEM

(71) Applicant: Hitachi, Ltd., Tokyo (JP)

(72) Inventors: Rintaro Fujimoto, Hitachinaka (JP); Yoshihiko Nagamine, Hitachi (JP); Masumi Umezawa, Mito (JP); Toru Umekawa, Hitachi (JP); Yusuke Fujii, Hitachi (JP); Hiroshi Akiyama, Hitachiota (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 14/318,881

(22) Filed: Jun. 30, 2014

(65) Prior Publication Data

US 2014/0316184 A1    Oct. 23, 2014

Related U.S. Application Data

(63) Continuation of application No. 14/055,921, filed on Oct. 17, 2013, now Pat. No. 8,796,648, which is a continuation of application No. 13/171,704, filed on Jun. 29, 2011, now Pat. No. 8,581,218.

(30) Foreign Application Priority Data

Jun. 30, 2010   (JP) ................. 2010-148471

(51) Int. Cl.
*A61N 5/00* (2006.01)
*G21G 5/00* (2006.01)
*A61N 5/10* (2006.01)

(52) U.S. Cl.
CPC .............. *A61N 5/103* (2013.01); *A61N 5/1043* (2013.01); *A61N 2005/1087* (2013.01)

(58) Field of Classification Search
CPC .. A61N 5/10; A61N 5/103; A61N 2005/1087
USPC ........ 250/492.3, 396 ML, 397, 396 R, 492.2, 250/492.22, 492.21, 492.1
See application file for complete search history.

(56) References Cited

U.S. PATENT DOCUMENTS 8,581,218 B2 * 11/2013 Fujimoto et al. ........... 250/492.3
8,796,648 B2 *  8/2014 Fujimoto et al. ........... 250/492.1

(Continued)

FOREIGN PATENT DOCUMENTS

JP       4273502 B2    3/2009
JP    2009-66106 A    4/2009

OTHER PUBLICATIONS van de Water, S. et al., "Tumor tracking with scanned proton beams: assessing the accuracy and practicalities", Physics in Medicine and Biology, vol. 54, No. 21, Nov. 7, 2009, p. 6549-6563.

*Primary Examiner* — David Porta
*Assistant Examiner* — Meenakshi Sahu
(74) *Attorney, Agent, or Firm* — Mattingly & Malur, P.C.

(57) ABSTRACT

In a particle therapy treatment planning system for creating treatment plan data, the movement of a target (patient's affected area) is extracted from plural tomography images of the target, and the direction of scanning is determined by projecting the extracted movement on a scanning plane scanned by scanning magnets. Irradiation positions are arranged on straight lines parallel with the scanning direction making it possible to calculate a scanning path for causing scanning to be made mainly along the direction of movement of the target. The treatment planning system can thereby realize dose distribution with improved uniformity.

10 Claims, 14 Drawing Sheets

(56) References Cited

U.S. PATENT DOCUMENTS

| | | |
|---|---|---|
| 2002/0128807 A1 | 9/2002 | Sakamoto et al. |
| 2006/0033042 A1* | 2/2006 | Groezinger et al. ........ 250/492.1 |
| 2010/0059688 A1* | 3/2010 | Claereboudt et al. ......... 250/397 |
| 2014/0046113 A1* | 2/2014 | Fujimoto et al. .................. 600/1 |

* cited by examiner

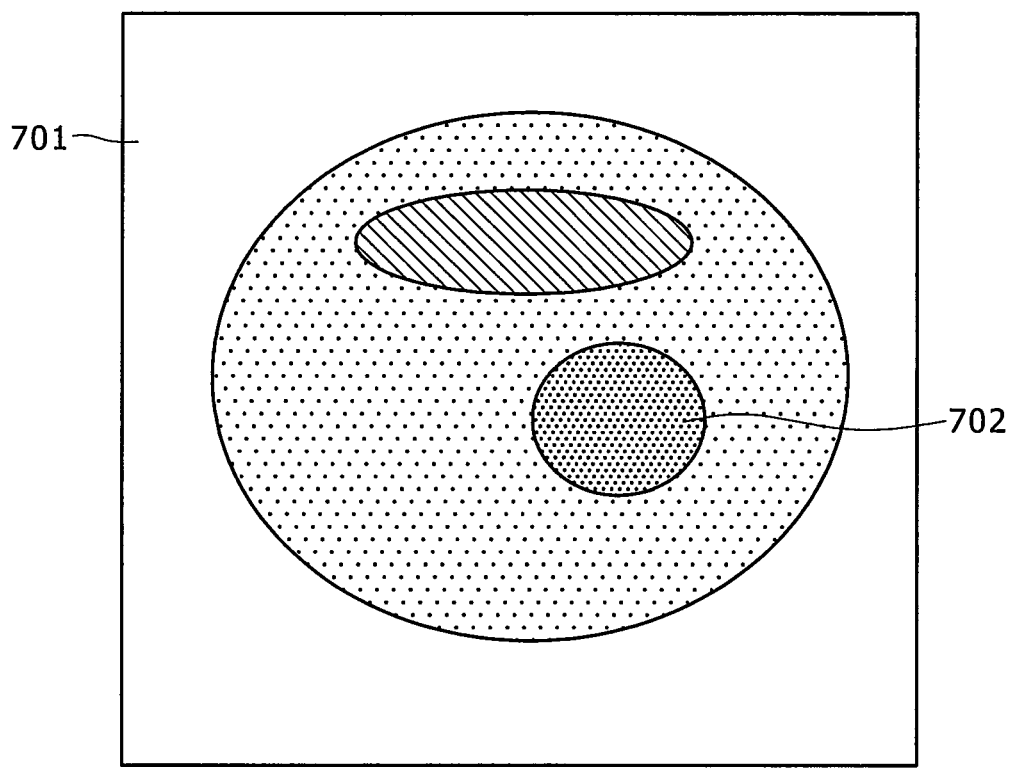
F I G . 7

US 9,012,873 B2

TREATMENT PLANNING SYSTEM, DEVICE FOR CALCULATING A SCANNING PATH AND PARTICLE THERAPY SYSTEM

CROSS-REFERENCE

This is a continuation application of U.S. application Ser. No. 14/055,921, filed Oct. 17, 2013, which is a continuation application of U.S. application Ser. No. 13/171,704, filed Jun. 29, 2011 (now U.S. Pat. No. 8,581,218), which claims priority to Japanese Patent Application No. 2010-148471 filed on Jun. 30, 2010. The entire disclosures of all of these applications are hereby incorporated by reference.

FIELD OF THE INVENTION

The present invention relates to a treatment planning system, a device for calculating a scanning path and a particle therapy system, particularly the particle therapy system for treating an affected area of a patient by irradiating the affected area with an ion beam of, for example, protons or carbon ions and the treatment planning system used for a particle therapy system.

BACKGROUND OF THE INVENTION

Particle therapy is conducted by irradiating target tumor cells with a particle beam. Among the radiant rays used in particle therapy, x rays are most widely used. Recently, however, demand has been rising for particle therapy in which particle rays (ion beam), typically a proton beam or a carbon ion beam capable of achieving high target dose conformity, are used.

In particle therapy, excessive irradiation or inadequate irradiation may cause adverse effects on normal tissues or may lead to recurrence of a tumor. It is therefore required to irradiate a target tumor region with an ion beam for a specified dose with maximum accuracy and conformity. In the field of particle therapy, use of a scanning irradiation method has been increasing so as to realize high dose conformity. In a scanning irradiation method, a fine ion beam is used to completely irradiate the inside of a tumor to achieve a high dose only on a tumor region. The scanning irradiation method does not basically require patient-specific devices such as a collimator for forming ion beam dose distribution into a tumor shape, so that it is possible to form dose distribution into various patterns.

In the scanning irradiation method, to irradiate an arbitrary position inside a tumor, it is necessary to control the depth to which an ion beam reaches (beam range) and the irradiation position on a plane perpendicular to the direction of beam travel (on a lateral plane). The range of an ion beam can be controlled by varying the beam energy using an accelerator or a range shifter. The irradiation position on a lateral plane can be arbitrarily controlled by bending the direction of beam travel using two sets of scanning magnets.

In the scanning irradiation method, unlike in cases where an entire tumor is irradiated with spread x-rays at a time, divided regions of a tumor are irradiated with a beam in turn. Therefore, when a beam is irradiated to a target which moves, for example, due to respiration or heart beat, the relative distance between irradiation positions changes to differ from the distance assumed at the time of planning, possibly making a planned dose distribution unavailable. In a method used to avoid the above problem, movement of an irradiation target is observed and an ion beam is irradiated only when the target is in a specific position.

In other methods also proposed, reducing the difference between a planned dose distribution and a real dose distribution is attempted by controlling the number of times of irradiation or the scanning path. In the method proposed in Japanese Patent No. 4273502, for example, a same target position is irradiated plural number of times so as to average dose errors caused by movement of the target and thereby reduce the dose distribution error relative to a planned dose distribution. Furthermore, according to non-patent literature (S Water, R Kreuger, S Zenklusen, E Hug and A J Lomax, "Tumour tracking with scanned proton beams assessing the accuracy and practicalities," Phys. Med. Biol. 54 (2009) 6549-6563), aligning a main direction of ion beam scanning with the direction of target movement brings a real dose distribution closer to a planned dose distribution.

SUMMARY OF THE INVENTION

With existing treatment planning systems, it has been difficult to arbitrarily set an ion beam scanning direction. In existing treatment planning systems, a scanning direction is determined regardless of the direction of target movement as follows. Irradiation position control in lateral directions is performed using two sets of scanning magnets which scan an ion beam in mutually perpendicular directions. The speeds of scanning by the two scanning magnets are not the same. Generally, the scanning magnet positioned upstream along the direction of beam travel can perform scanning at a higher speed. A scanning path is formed such that, first, scanning is made in the direction of fast scanning by one of the scanning magnets until an end of the target is reached, then such that, after the scanning position is moved a little in the direction of scanning by the other scanning magnet, fast scanning is resumed in the direction of fast scanning. Generally, this process is repeated to form a zig-zag scanning path. This type of scanning path is formed, for example, in the method disclosed in Japanese Unexamined Patent Application Publication No. 2009-66106.

To scan an ion beam in the same direction as the direction of target movement, the treatment planning system to be used is required to grasp the movement of a target and determine a scanning direction which coincides with the direction of target movement. Since an ion beam can be irradiated to a patient from an arbitrary direction by an irradiation device, the scanning direction has to be determined by taking into consideration the direction of beam irradiation even when the movement of the target is unchanged. For the operator of a treatment planning system, determining a scanning direction in such a situation is difficult.

As described above, existing treatment planning systems and devices for calculating s scanning path do not provide any means by which the operator can specify, in a simple manner, a scanning direction taking into consideration three-dimensional movement of a target and a specified irradiation direction.

The above problem can be solved by the feature of the independent claims. The dependent claims relate to advantageous embodiments of the invention. A treatment planning system for creating a treatment plan for particle therapy can comprising: an input device; an arithmetic device for performing arithmetic processing based on a result of input to the input device and creating treatment plan information (scanning path information); and a display device for displaying the treatment plan information. In the treatment planning system, the arithmetic device calculates a scanning path by setting a pre-specified optional direction as a main direction for scanning irradiation positions with an ion beam using a scanning magnet.

The arithmetic device calculates: based on multiple tomography images of multiple states of a target region, a position of a specific region; extracts a direction of movement of the position of the specific region; and applies the direction extracted and projected on an ion beam scanning surface as the direction of movement of the target.

With the device for calculating a scanning path according to the invention it is possible to realize a dose distribution of a very high uniformity in the irradiation target area. According to the present invention, treatment planning data which can realize dose distribution with improved uniformity can be created.

BRIEF DESCRIPTION OF THE DRAWINGS

FIG. 7 is a diagram illustrating input of a target region in a slice of CT data;

DETAILED DESCRIPTION OF THE PREFERRED EMBODIMENTS

Embodiments of the present invention will be described below with reference to drawings.

First Embodiment

A treatment planning system (or a scanning path creation system) according to a preferred embodiment of the present invention will be described below with reference to drawings. First, a particle therapy system for which the treatment planning system is used will be described with reference to FIGS. 3 and 4.

Figure 3:
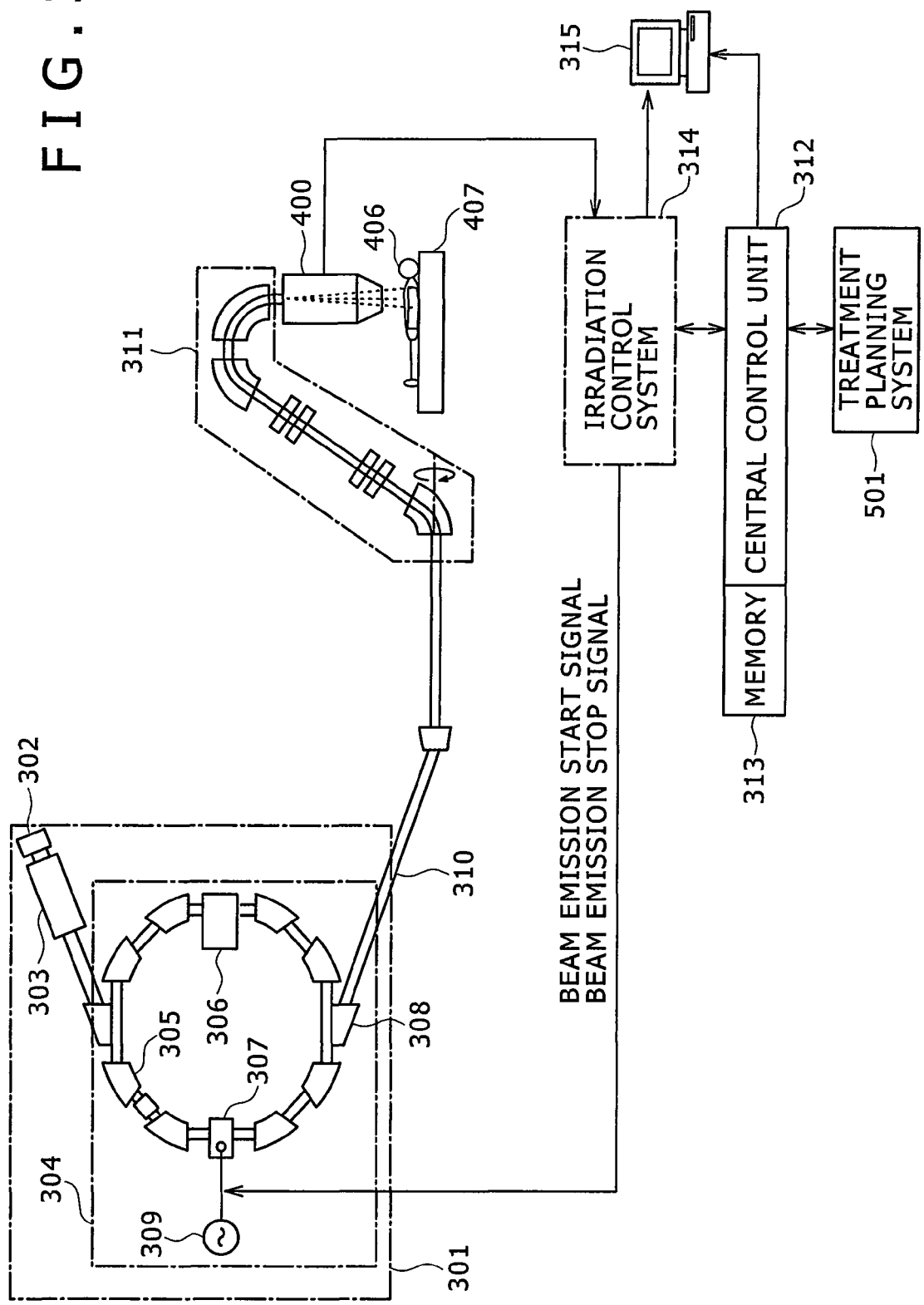
FIG. 3 is a diagram illustrating an overall structure of a particle therapy system.

FIG. 3 shows an overall structure of the particle therapy system. An ion beam generator 301 includes an ion source 302, a preaccelerator 303, and an ion beam accelerator 304. Even though the ion beam accelerator of the present embodiment is assumed to be a synchrotron-type ion beam accelerator, the present embodiment is also applicable to other types of ion beam accelerators including cyclotron-type accelerators. The synchrotron-type ion beam accelerator 304 includes, as shown in FIG. 3, a bending magnet 305, an accelerator 306, an extraction radiofrequency device 307, an extraction deflector 308, and a quadruple magnet (not shown) which are arranged along the beam orbit thereof.

With reference to FIG. 3, how an ion beam generated by the ion beam generator 301 making use of the synchrotron-type ion beam accelerator 304 is emitted toward a patient will be described below. The ion particles (for example, protons or heavy ions) supplied from the ion source 302 are accelerated by the preaccelerator 303 and is sent to the synchrotron 304 that is a beam accelerator. The synchrotron 304 includes the accelerator 306. The accelerator 306 accelerates the ion beam by applying a radiofrequency wave to a radiofrequency acceleration cavity (not shown) provided in the accelerator 306 in synchronization with the period at which the ion beam circling inside the synchrotron 304 passes the accelerator 306. The ion beam is accelerated in this way until it reaches a predetermined energy level.

When, after the ion beam is accelerated to a predetermined energy level (for example, 70 to 250 MeV), an emission start signal is outputted from a central control unit 312 via an irradiation control system 314, radiofrequency power from a radiofrequency power supply 309 is applied, by an extraction radiofrequency electrode installed in the extraction radio frequency device 307, to the ion beam circling in the synchrotron 304, causing the ion beam to be emitted from the synchrotron 304.

A high energy beam transport line 310 connects the synchrotron 304 and a beam delivery system (nozzle) 400. The ion beam extracted from the synchrotron 304 is led, via the high energy beam transport line 310, to the beam delivery system 400 installed at a gantry 311. The gantry 311 is for allowing an ion beam to be irradiated onto a patient 406 from an arbitrary direction. The gantry 311 can rotate, in its entirety, into any direction around a bed 407 on which the patient 406 lies.

The beam delivery system 400 is for shaping the ion beam to be finally irradiated onto the patient 406. Its structure differs depending on the irradiation method employed. A passive scattering method and a scanning method are among typical irradiation methods. The present embodiment uses the scanning method. In the scanning method, a fine ion beam transported through the high energy beam transport line 310 is irradiated as it is onto a target and is scanned three-dimensionally making it possible to consequently form a high dose region on the target only.

Figure 4:
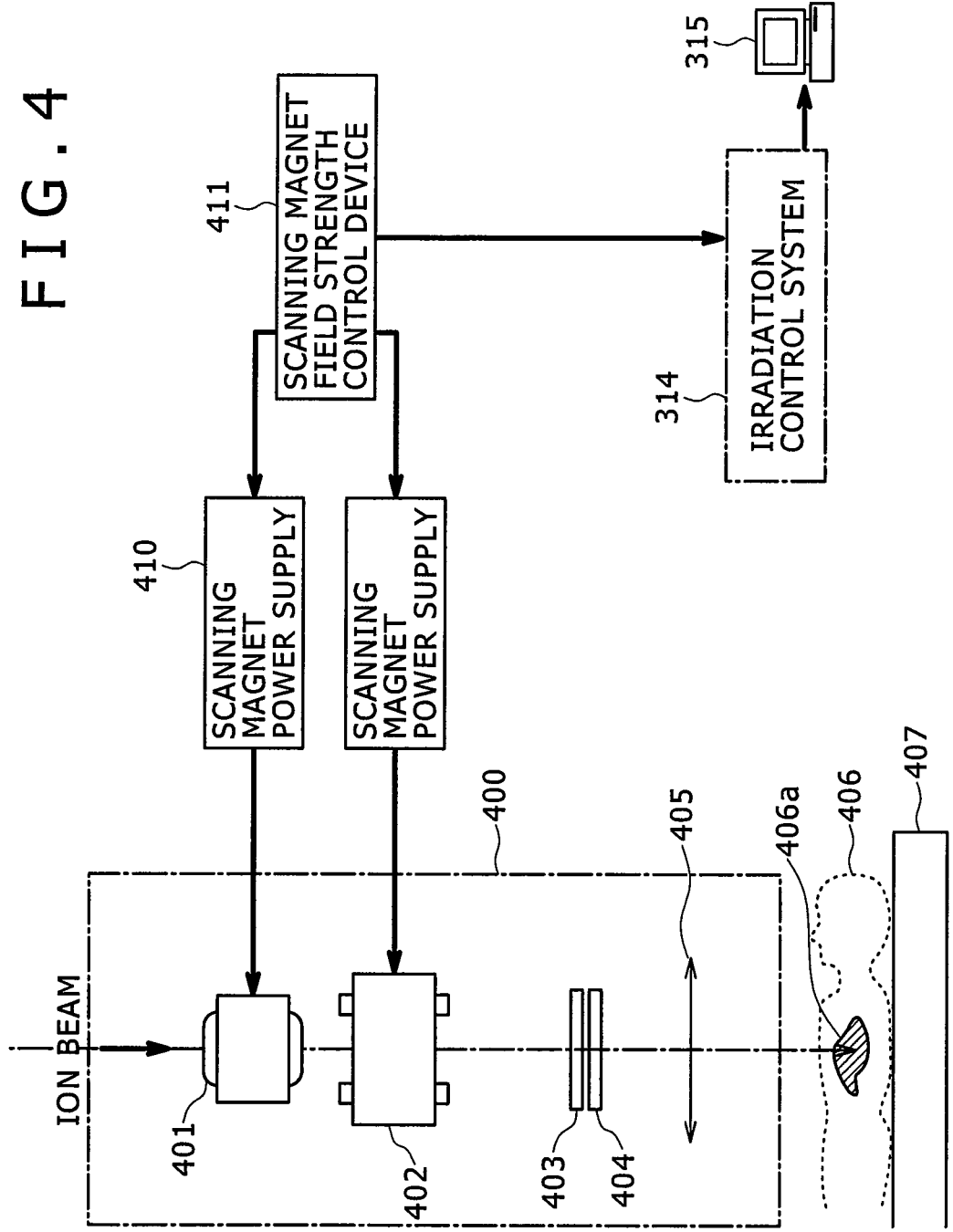
FIG. 4 is a diagram illustrating a structure of a beam delivery system.

FIG. 4 shows a structure of the beam delivery system 400 employing the scanning method. The roles and functions of components of the beam delivery system 400 will be briefly described below with reference to FIG. 4. The beam delivery system 400 is provided with scanning magnets 401 and 402, a dose monitor 403, and a beam position monitor 404 arranged in the mentioned order from the upstream side. The dose monitor measures the amount of the ion beam passing therethrough. The beam position monitor can measure the position passed through by the ion beam. The information provided by these monitors enables the irradiation control system 314 to perform control to keep the ion beam irradiated to a predetermined position in a predetermined amount.

The direction of travel of the fine ion beam transported from the ion beam generator 301 through the high energy beam transport line 310 is bent by the scanning magnets 401 and 402. These scanning magnets are provided so as to cause magnetic flux lines to be generated perpendicularly to the direction of travel of the ion beam. Referring to FIG. 4, for example, the scanning magnet 401 bends the ion beam in a scanning direction 405 and the scanning magnet 402 bends the ion beam perpendicularly to the scanning direction 405. Using these two scanning magnets, the ion beam can be moved to an arbitrary position in a plane perpendicular to the direction of travel thereof so as to irradiate a target 406a.

The irradiation control system 314 controls, via a scanning magnet field strength control device 411, the amounts of current applied to the scanning magnets 401 and 402. The scanning magnets 401 and 402 have currents supplied from scanning magnet power supplies 410 allowing magnetic fields of strengths corresponding to the amounts of currents supplied to be generated so as to arbitrarily set the degree of bending of the ion beam. The relationships between the ion beam, degree of beam bending, and amounts of currents are held as a table in a memory 313 included in the central control unit 312 to be referred to as required.

When the scanning method is used for ion beam irradiation, an ion beam can be scanned in two ways. In one way, discrete scanning is made in which an irradiation position is moved and stopped repeatedly. In the other way, an irradiation position is continuously changed. In discrete scanning, a predetermined amount of ion beam is irradiated at a fixed position which is referred to as a spot. Supply of the ion beam is then suspended and the amounts of currents applied to the scanning magnets are changed so as to move the irradiation position. After the irradiation position is moved, irradiation of the ion beam is resumed. When, in this process, high-speed scanning is possible, the ion beam need not necessarily be suspended.

In the method in which the ion beam irradiation position is continuously moved, the irradiation position is changed while irradiation of the ion beam is maintained. Namely, the irradiation position is changed by continuously changing the degrees of excitation of the scanning magnets while the ion beam irradiation is maintained so as to scan the entire part of the irradiation field. In this method, the irradiation amount can be changed over different irradiation positions by changing either or both of the speed of scanning effected by the scanning magnets and the amount of ion beam current.

Figure 5:
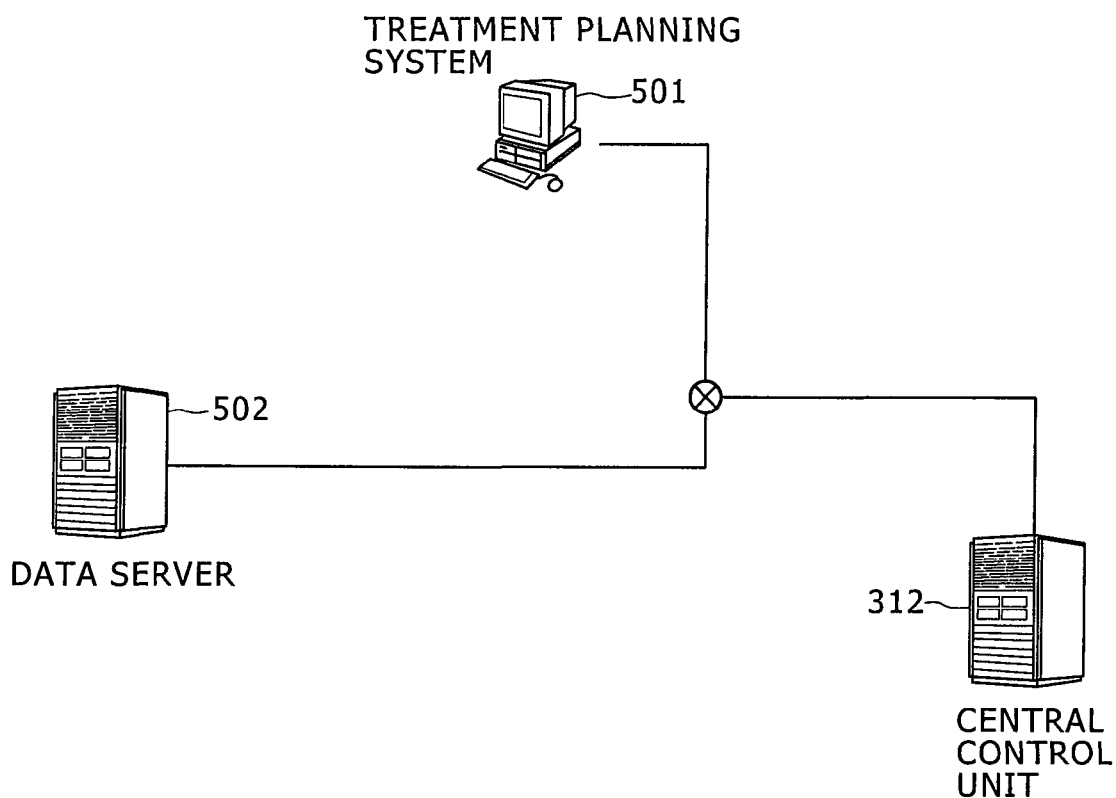
FIG. 5 is a diagram illustrating a configuration of a control system including the treatment planning system according to the first embodiment.
Figure 6:
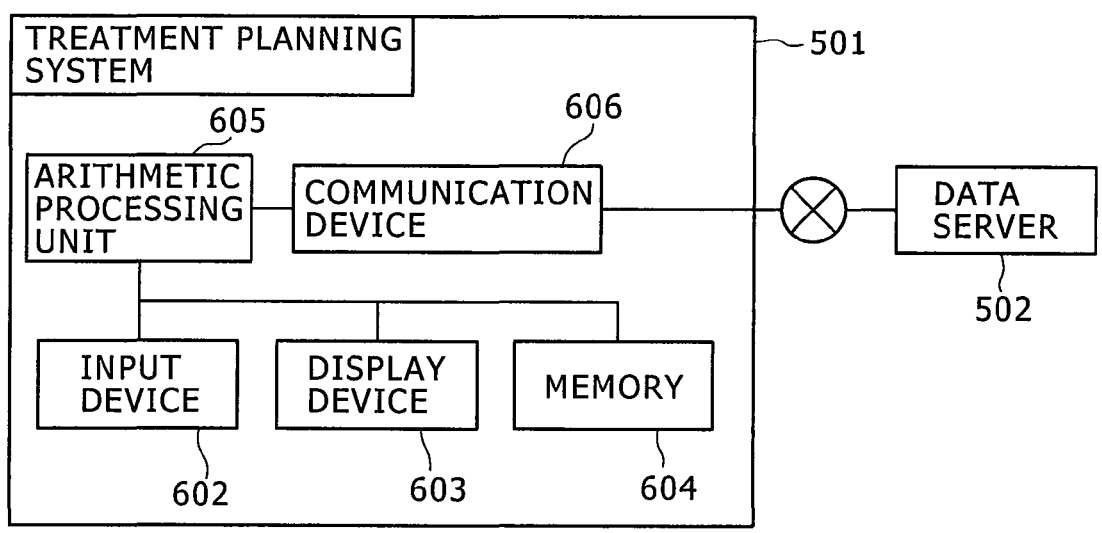
FIG. 6 is a diagram illustrating a structure of the treatment planning system according to the first embodiment.

A treatment planning system according to a preferred embodiment of the present invention will be described below with reference to FIG. 5. A treatment planning system 501 is connected, via network, to a data server 502 and the central control unit 312. The treatment planning system 501 includes, as shown in FIG. 6, an input device 602, a display device 603, a memory 604, an arithmetic processing unit 605, and a communication device 606. The arithmetic processing unit 605 is connected to the input device 602, display device 603, memory (storage device) 604, and communication device 606.

Prior to treatment, images for use in treatment planning are taken. As images used for treatment planning, computed tomography (CT) data is most popular. CT data used for treatment planning is three-dimensional data composed using images of a patient taken by irradiation from plural directions. With image taking growing higher in speed recently, computed tomography makes it possible to acquire plural sets of CT data on plural states (referred to as phases) of even a patient's site periodically moving due to respiration by taking plural images of the site in different phases caused by respiratory movement. This computed tomography is referred to as four-dimensional computed tomography (4DCT). 4DCT imaging makes it possible to observe movement due to, for example, respiration of a target by comparing CT data on different phases of the site. When using such a method, to make movement of the target observable with increased accuracy, a marker such as a metal ball may be implanted in the target.

Figure 1:
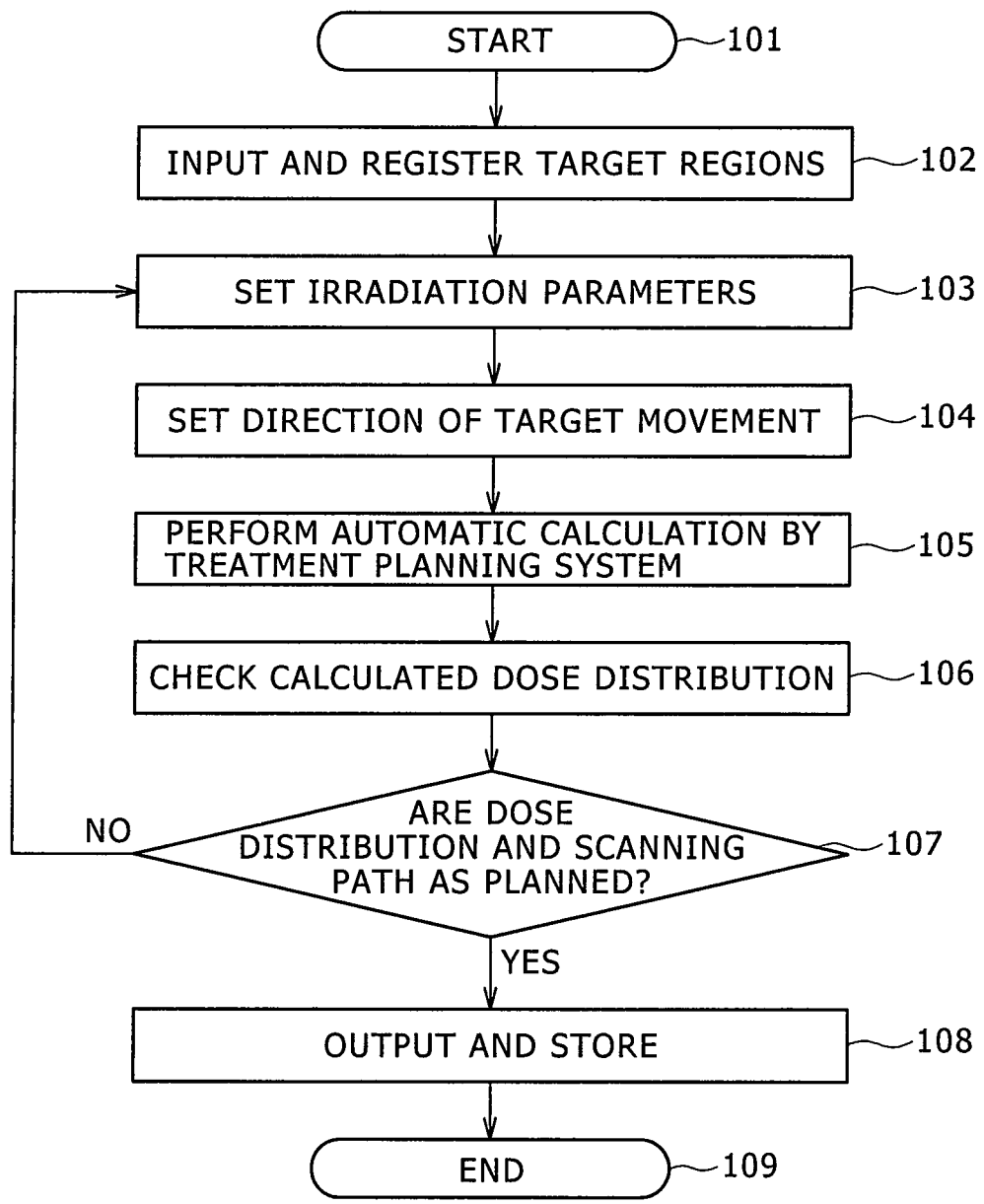
FIG. 1 is a flowchart for treatment planning according to a preferred embodiment of the present invention.

CT data taken using a CT system (not shown) is stored in the data server 502. The treatment planning system 501 uses the CT data. FIG. 1 is a flowchart for treatment planning. When treatment planning is started (step 101), the treatment planning system 501 reads required CT data from the data server 502 in accordance with instructions from a medical physicist (or doctor) operating the treatment planning system 501. Namely, the treatment planning system 501 copies (stores) the CT data from the data server 502 to the memory 604 via the network connected to the communication device 606.

When the CT data has been read, the operator, while checking the CT data displayed on the display device 603, inputs data on a region to be specified as a target for each slice of the CT data using the input device 602 that may be, for example, a mouse. When, like in the case of 4DCT, there are plural data sets acquired by imaging a same site, an image may be synthesized from plural images and the above target selection operation may be performed using the synthesized image. A set of synthesized image can be obtained, for example, by comparing the CT values of each set of corresponding spots, each representing a same position, of plural images and selecting a highest luminance value for each position.

When region data has been inputted for each slice of the CT data, the operator registers the inputted regions in the treatment planning system (step 102) causing the regions inputted by the operator to be stored as three-dimensional position information in the memory 604. In cases where there are other regions to be also assessed and controlled, for example, when there are critical organs requiring doses on them to be minimized, the operator also registers the positions of such critical organs. FIG. 7 shows a state with a target region 702 inputted, by an operator using the display device 603, on a slice 701 including CT data.

Next, the operator specifies the direction of irradiation that is determined by the angles of the gantry 311 and bed 407. For irradiation from plural directions, specify plural sets of angles. The other parameters to be determined by the operator to perform ion beam irradiation include the dose (prescription dose) to be irradiated on each region registered in step 102 and the distance between adjacent spots. The prescription doses to be determined as irradiation parameters also include, besides the dose to be irradiated on each target, a tolerable dose for each critical organ. The distance between adjacent spots is initially determined automatically to be approximately the same as the beam size of the ion beam, but it can be changed by the operator. The operator is required to set these irradiation parameters (step 103).

Figure 8:
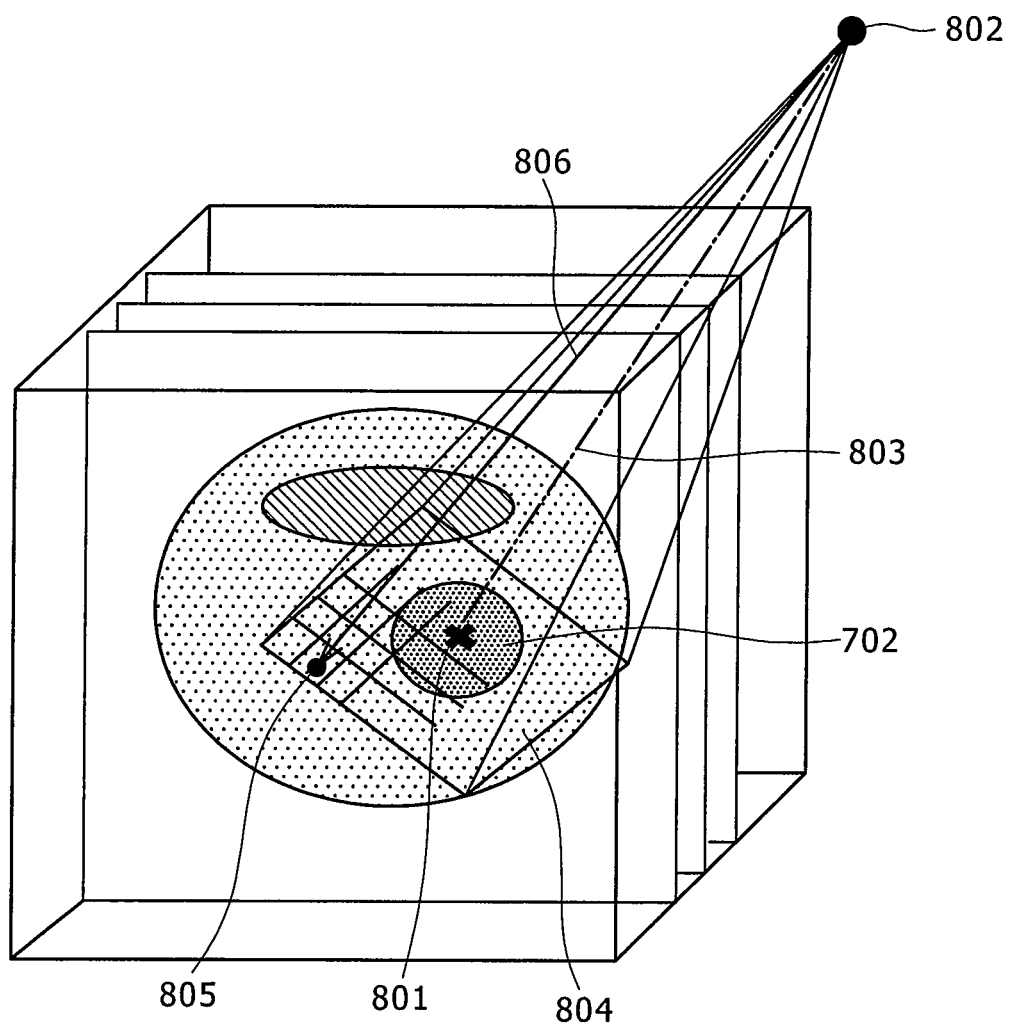
FIG. 8 is a conceptual diagram illustrating beam irradiation by a scanning method.

In addition to the above parameters, the direction of target movement is specified using a feature function of the treatment planning system according to the present embodiment. How to specify the direction of target movement will be described below with reference to FIGS. 8 and 9. As shown in FIG. 8, for ion beam irradiation, the gravitational center of the target region 702 is assumed to be positioned to coincide with an isocenter (rotational center of the gantry 311) 801. A spot position is defined on coordinates in a plane (isocenter plane) 804 perpendicular to a straight line (beam center axis) 803 which includes the isocenter 801 and connects a scanning center (beam source) 802 and the isocenter 801. In the following, the plane 804 will be referred to as the isocenter plane and the straight line 803 will be referred to as the beam center axis. For example, when there is a spot at position 805 on the isocenter plane 804, the currents applied to the scanning magnets 401 and 402 are adjusted to make the ion beam pass the position 805 on the isocenter plane 804. As a result, the trajectory of the ion beam becomes like a straight line 806. How far the ion beam reaches depends on the beam energy.

Figure 9:
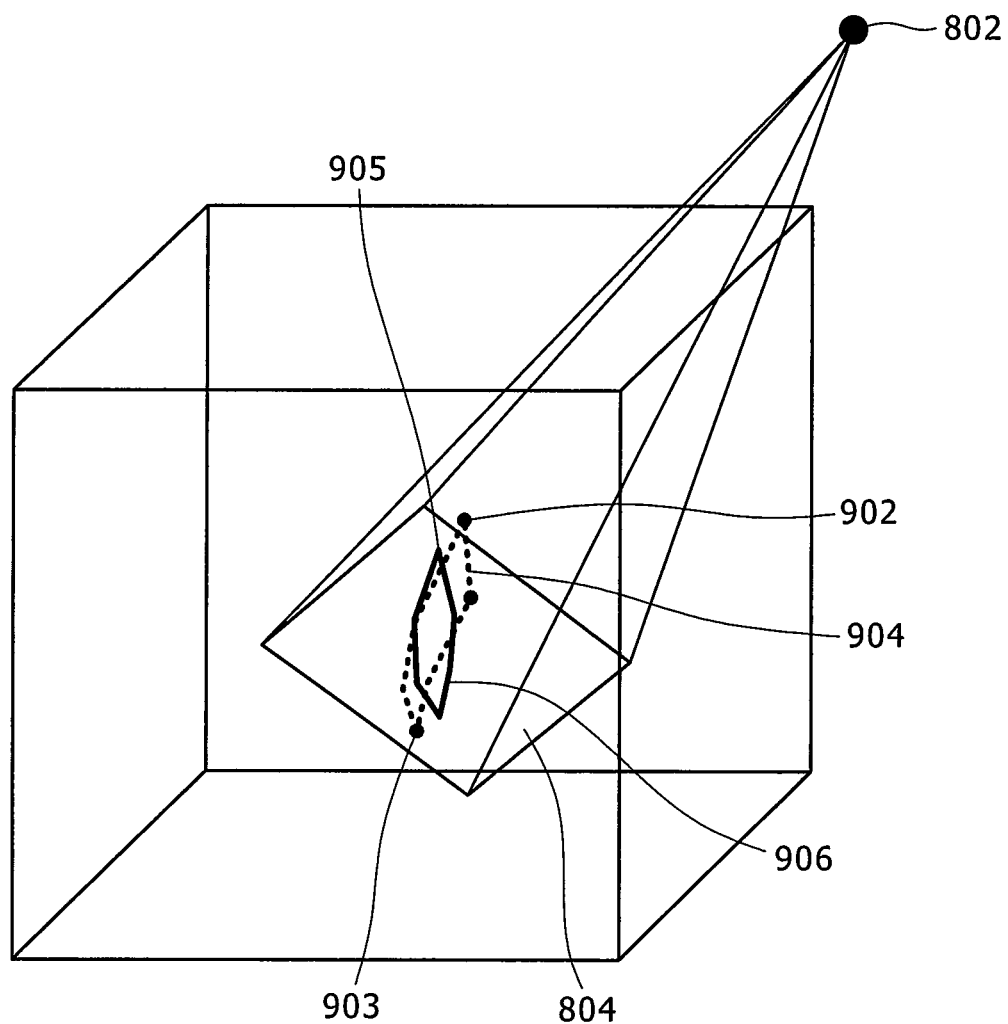
FIG. 9 is a diagram illustrating a process of calculating a direction of target movement according to the first embodiment.

The following description will be based on an example case in which 4DCT data is taken making use of an implanted marker. Effects similar to those generated in the following example case can also be obtained without using any marker by having an arbitrary feature point in an image specified by the operator. The treatment planning system 501 searches all CT slice images provided by the 4DCT data for each phase stored in the memory 604 and determines a marker position in each slice. This may be done directly by the operator when automatic searching is difficult. Consequently, the marker position in the CT data for each phase is determined. This process is illustrated in FIG. 9. In FIG. 9, points 902 and 903 each represent a marker position in a phase. Linearly connecting the marker positions in all phases determines a three-dimensional marker trajectory 904. The marker is positioned such that the marker trajectory represents movement of a target.

Next, the marker positions, including the points 902 and 903, in all phases are projected on the isocenter plane 804. In FIG. 9, point 905 represents the point 902 projected on the isocenter plane 804. Thus, projecting all marker positions on the isocenter 804 determines a marker trajectory 906 projected on the isocenter plane 804.

Figure 10:
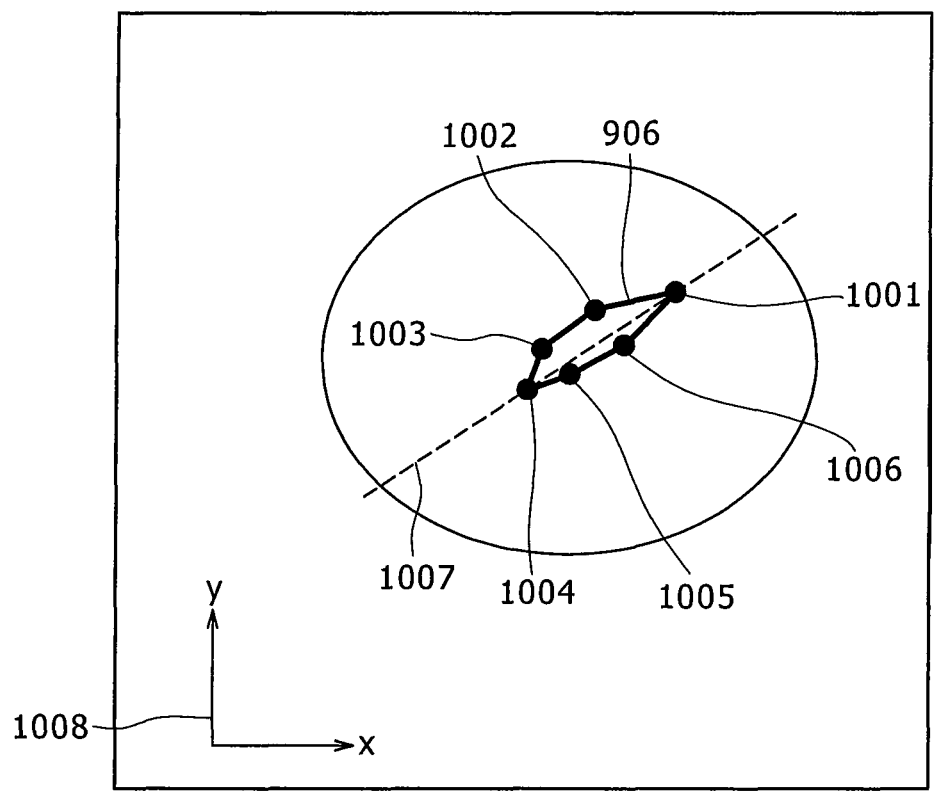
FIG. 10 is a diagram illustrating a process of calculating a direction of target movement according to the first embodiment.

The projection result is displayed on the display device 603 of the treatment planning system 501. This is illustrated in FIG. 10. Points 1001, 1002, 1003, 1004, 1005, and 1006 represent the marker positions in corresponding phases projected on the isocenter plane 804. Based on the displayed marker positions, the arithmetic processing unit 605 of the treatment planning system 501 automatically calculates the direction of target movement. For example, the arithmetic processing unit 605 calculates the distances between multiple points 1001 to 1006 and determines two points, the distance between which is larger than the distance between any other combined two points. In the case of the example shown in FIG. 10, points 1001 and 1004 are selected as the two points most spaced apart and the direction along line 1007 connecting points 1001 and 1004 is defined as the direction of target movement. In cases where an ion beam is emitted only when the marker is inside a specific region, it is possible to extract only the points corresponding to the phases with the marker in such a specific region and perform calculations as described above.

Figure 11:
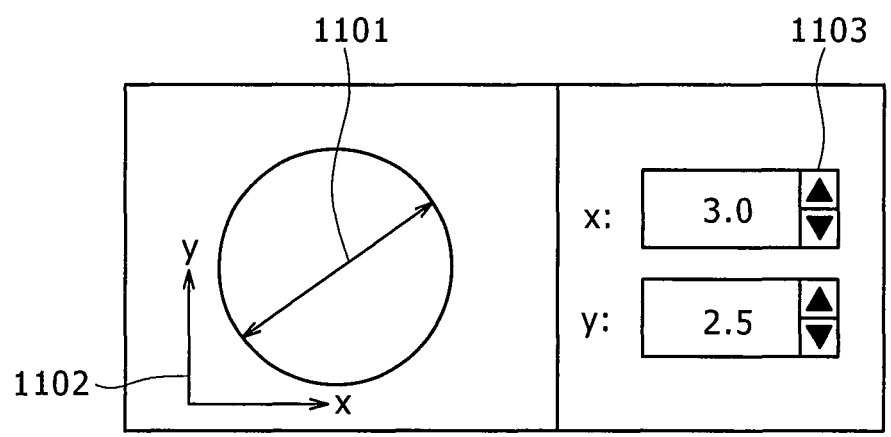
FIG. 11 is a diagram illustrating a screen for specifying a direction of target movement by a method according to the first embodiment.

The direction of target movement determined by calculation is also displayed on the display device 603 of the treatment planning system 501. An example of the direction display is shown in FIG. 11. In FIG. 11, an arrowed direction 1101 represents the calculated direction of target movement. This display appears together with a display of the isocenter plane 804 shown in FIG. 10. Or, the arrow 1101 may be displayed overlapped with a display like the one shown in FIG. 10. The coordinate systems 1008 shown in FIGS. 10 and 1102 shown in FIG. 11 both used to define directions are common. The operator can manually modify, as required, the direction referring to the coordinate systems. Namely, the direction can be changed by inputting, on the input screen 1103, an x-direction component and a y-direction component of the arrow 1101. It is also possible to directly change the arrow direction on the display screen using an input device such as a mouse (step 104).

The direction of target movement may be determined after marker positions are projected on a plane as described above, but it may also be determined without projecting marker positions. Namely, referring to FIG. 9, out of all the points including points 902 and 903, two the distance between which is longer than the distance between any other combination of two points are selected and the direction along a line connecting the selected two points is determined as the direction of target movement. In the example case shown in FIG. 9, the direction along a line connecting points 902 and 903 is determined as the direction of target movement. Projecting the direction thus determined on the isocenter plane 804 determines the direction of target movement on the isocenter plane.

An advantage of the above method of determining the direction of target movement without projecting marker positions on a plane is that components of target movement in a direction perpendicular to the isocenter plane 804 can also be calculated. The dose distribution caused by an ion beam becomes a Gaussian-like distribution along a direction perpendicular to the direction of travel of the ion beam. The dose distribution along the direction of travel of the ion beam, however, shows a sharp peak immediately before the ion beam stops. Generally, therefore, the movement of a target along the direction of travel of the ion beam, i.e. a direction perpendicular to the isocenter plane 804, affects the dose distribution more than the movement of a target along a lateral direction. When the component of target movement in a direction perpendicular to the isocenter plane 804 is also displayed on the display screen shown in FIG. 11, the operator can modify the direction of beam irradiation that is determined by the angles of the gantry 311 and bed 407 so as to make the component of target movement perpendicular to the isocenter plane 804 smaller than a maximum allowable value.

Figure 2:
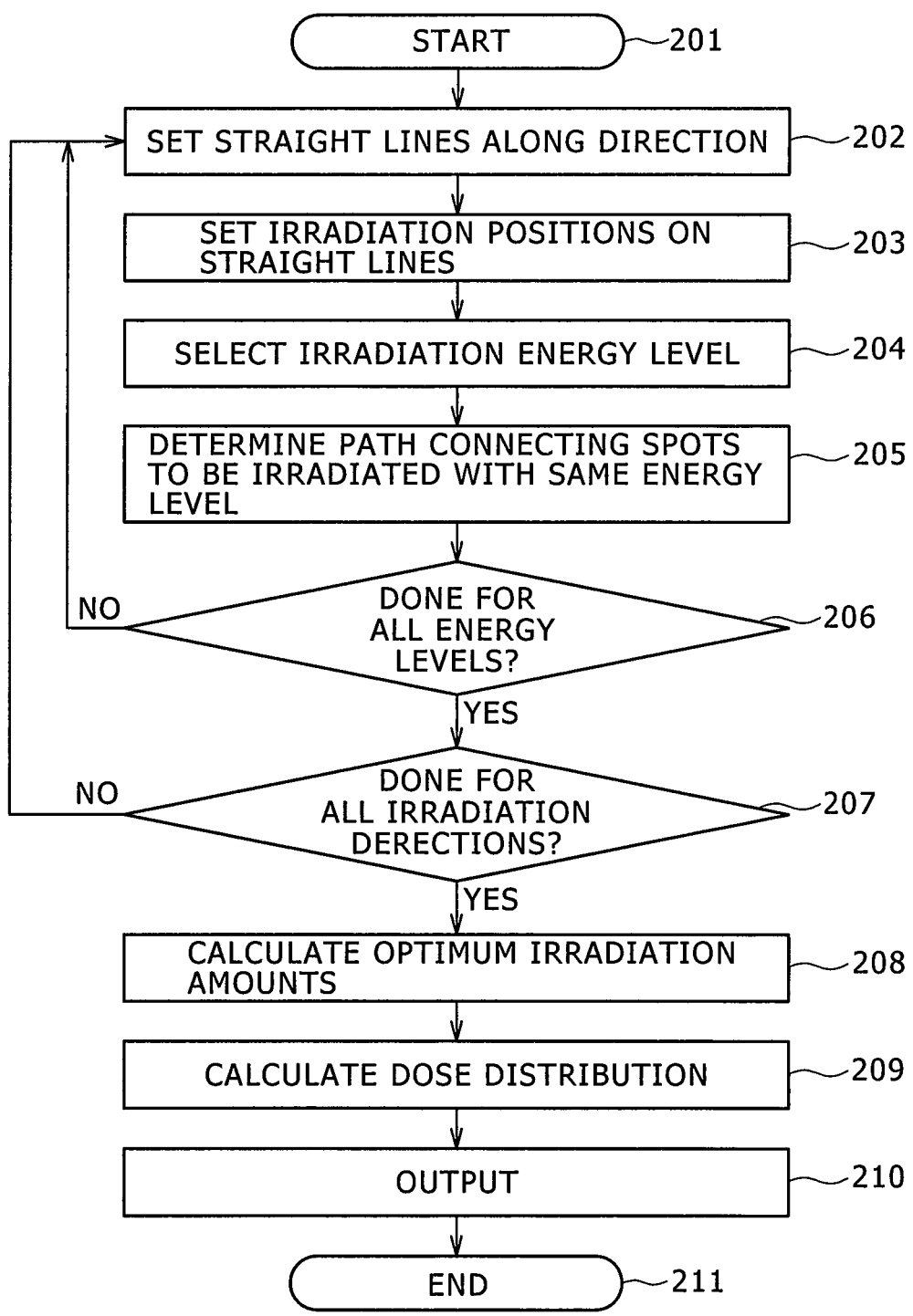
FIG. 2 is a flowchart for treatment planning by a treatment planning system according to a first embodiment of the present invention.

After the above parameters are determined, the treatment planning system 501 automatically performs calculations (step 105). In the following, details of calculations the treatment planning system 502 performs following the flowchart shown in FIG. 2 will be described.

First, the treatment planning system 501 determines positions to be irradiated with an ion beam. In cases where a discrete scanning method is used, discrete spot positions are calculated. In cases where an ion beam is to be irradiated continuously, a scanning path is calculated. Even though, the following description of the present embodiment is based on a discrete scanning method, a continuous scanning method may also be used. Effects similar to those of the present embodiment can also be obtained using a continuous scanning method which can be regarded as a method in which discrete positions to be irradiated with an ion beam are very closely arranged along a scanning path. When plural irradiation directions (determined by the angles of the gantry 311 and bed 407) are specified, the operation performed for a single irradiation direction is repeated for the plural irradiation directions.

The treatment planning system 501 starts selecting spot positions based on the CT data stored in the memory 604 and the region information inputted by the operator (step 201). As described in the foregoing, the positions to be irradiated with an ion beam are determined on the coordinates on the isocenter plane 804. Referring to FIG. 8, assume that the point 805 on the isocenter plane 804 is selected as a position to be irradiated. The treatment planning system 501 seeks an energy level which, when an ion beam is irradiated along the straight line 806 connecting the beam source 802 and point 805, causes the ion beam to stop approximately in a target range and selects the energy level (not necessarily singular) for use in irradiating the point 805. This process for energy level selection is performed for every irradiation position set on the isocenter plane. As a result, the combinations of positions to be irradiated on the isocenter plane and energy levels to be used are determined. In this way, the spots to be actually irradiated with an ion beam are determined.

Figure 12:
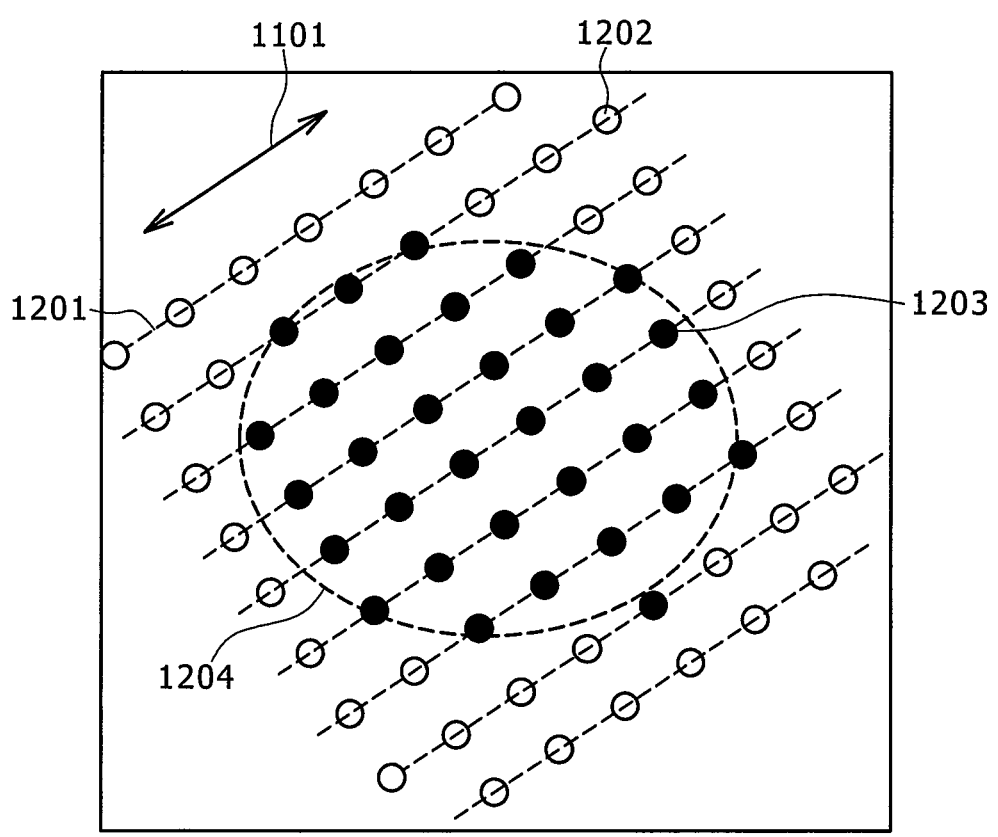
FIG. 12 is a diagram illustrating how to calculate spot positions.

On the isocenter plane 804, the positions to be irradiated are selected such that the distance between adjacent positions does not exceed the value specified in step 103. In an easiest way, positions may be arranged to form a square lattice such that positions mutually adjacent along a side are spaced apart from each other by a predetermined distance along the side. The treatment planning system 501 of the present embodiment can select the direction determined in step 104 as the axis of the above lattice, i.e. as the direction along which the positions to be irradiated are linearly arranged. FIG. 12 is a conceptual illustration of the process leading to selection of spots. The direction 1101 determined in step 104 is also shown in FIG. 12.

The treatment planning system 501 first sets plural straight lines parallel with the direction 1101 (step 202). Straight line 1201 represents one of the plural straight lines. The straight lines are spaced apart by the distance selected in step 103. Next, irradiation positions are set on each of the plural straight lines (step 203). The distance between irradiation positions adjacent to each other on a same straight line equals the distance between straight lines adjacent to each other. In FIG. 12, the irradiation positions thus set, including 1202 and 1203, are circularly represented, and it is seen that they are arranged to form a square lattice with its axis represented by the direction 1101. Finally, a beam energy level which causes, when the irradiation positions are irradiated with an ion beam, the ion beam to stop inside the target range is selected (step 204). The irradiation positions for which the ion beam stops outside the target range are not irradiated with the ion beam. Referring to FIG. 12, the irradiation positions, including 1202, represented by white circles are not irradiated with the ion beam. Only the irradiation positions, including 1203, represented by black circles, are irradiated with the ion beam. Broken line 1204 represents the target range contour at the depth where the ion beam of a certain energy level stops.

In cases where scanning is performed discretely and ion beam emission is suspended during the time after a spot is irradiated with an ion beam until the next spot starts being irradiated, the consequential dose distribution is not dependent on the scanning path. In such cases, the scanning path may be determined after the dose is determined for each spot. In the present embodiment, however, the scanning path is determined at this stage with consideration that, when a different scanning method is adopted, it becomes necessary to calculate dose distribution taking into consideration the scanning path. Namely, in the present embodiment, the scanning path is determined in step 205 regardless of the scanning method to be used.

Figure 13:
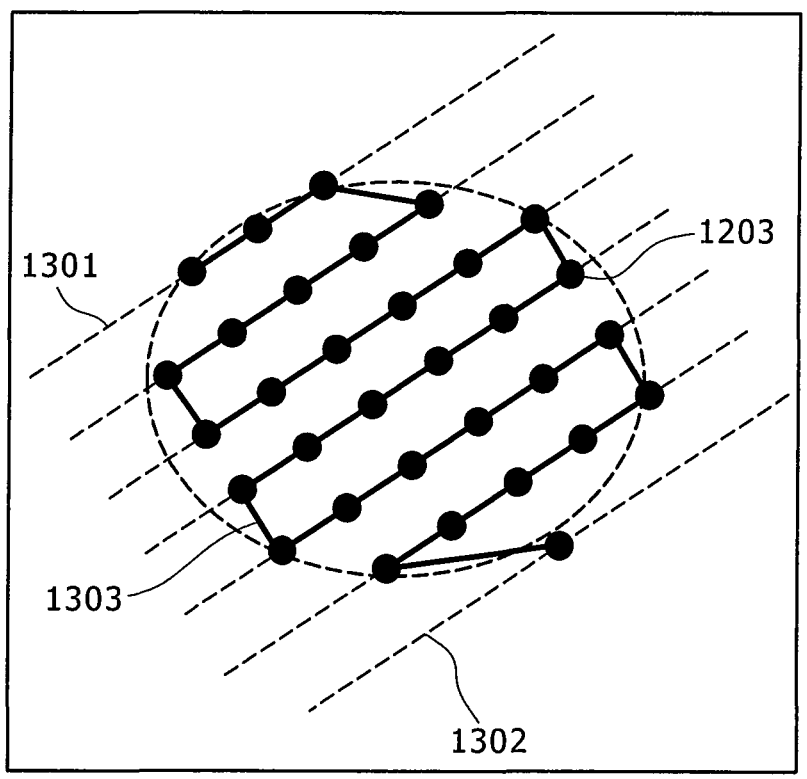
FIG. 13 is a diagram illustrating a scanning direction calculated by a method according to the first embodiment.

The scanning path is determined to be along the straight lines set in step 202. Referring to FIG. 13, the spots, including point 1203, to be irradiated with a certain beam energy level are represented by black circles. The scanning path begins with the straight line 1301 that is the top line among the straight lines set to be parallel with the direction defined by the operator. The ion beam scanning advances from spot to spot first along the straight line 1301. When the last spot on the straight line 1301 is reached, scanning moves to the next straight line adjacent to the straight line 1301 and the direction of scanning is reversed. This process is repeated until all the spots on straight line 1302 have been scanned. Consequently, the scanning path is zigzagged as indicated by arrow 1303.

The operation for determining a scanning path is performed for the spots to be irradiated with each of the selected beam energy levels. When the operation is completed for every energy level, the scanning paths for all spots to be irradiated have been determined (step 206). This is repeated for every irradiation direction in cases where irradiation is to be made in plural directions (step 207).

When all spot positions and a scanning path for them have been determined, the treatment planning system 501 starts calculation for irradiation amount optimization (step 208). This calculation determines the irradiation amount for each spot so as to approach the target dose distribution set in step 103. For this type of calculation, an objective function is widely made use of. The objective function represents an error quantified relatively to a target dose distribution determined using spot-by-spot irradiation amounts as parameters. The objective function is defined such that its value is smaller when the target dose distribution is approached closer. An irradiation amount for each spot which minimizes the function value is sought by iterative calculation and is determined as an optimum irradiation amount.

When the irradiation amount for each spot has been determined through iterative calculation, the treatment planning system 501 calculates dose distribution based on the finalized spot positions and spot irradiation amounts (step 209). The calculation results are displayed on the display device 603 (step 210). The operator checks the calculation results and determines whether the dose distribution meets the target conditions. Not only the dose distribution but also the spot positions and scanning path calculated by the treatment planning system 501 can also be checked on the display device 603 (step 106). When the dose distribution or the scanning path is found undesirable, the operator returns to step 103 and changes the settings of irradiation parameters such as the irradiation direction, prescription dose, or distance between spots.

Even when the operator returns to step 103 and changes parameter settings, the direction of target movement determined in step 104 is retained. According to the new conditions specified by the operator, the scanning path and the dose distribution are updated through steps 201 and 209, and the new results are displayed on the display device 603. When the displayed results are determined desirable, treatment planning is finished (step 107). The irradiation conditions acquired are stored, via network, in the data server 502 (steps 108 and 109).

When irradiating an ion beam, the central control unit 312 reads the corresponding treatment planning data stored in the data server 502. If necessary at that time, the data can be converted into a format readable by the central control unit 312. The central control unit 312 specifies conditions for ion beam irradiation such as the ion beam energy to be irradiated, scanning positions, and irradiation amounts. The irradiation control system 314 irradiates an ion beam based on the conditions specified by the central control unit 312.

According to the present embodiment, it is possible to input movement of a patient's affected area and generate treatment planning data to cause an ion beam to be scanned mainly in a direction coinciding with the direction of the movement, so that treatment planning data which can realize dose distribution with improved uniformity can be provided.

Second Embodiment

Even though, in the first embodiment, the direction of target movement is extracted using 4DCT images, effects similar to those of the first embodiment can also be obtained according to a second embodiment of the invention by having the direction of target movement directly specified by the operator using ordinary CT data without using any 4DCT image. The second embodiment will be described below.

The operation according to the second embodiment is the same as in the first embodiment up to step 103 shown in FIG. 1. The operation differing from the first embodiment will be described in the following. In the second embodiment, the direction of target movement is determined, in step 104, by the operator without using any 4DCT data. In cases where the direction of movement of a specific organ caused, for example, by respiration or heart beat is not considered to vary much, the operator may directly specify the direction of target movement without checking the target position, for example, using a marker, i.e. saving the operation for extracting the direction of target movement.

Figure 14:
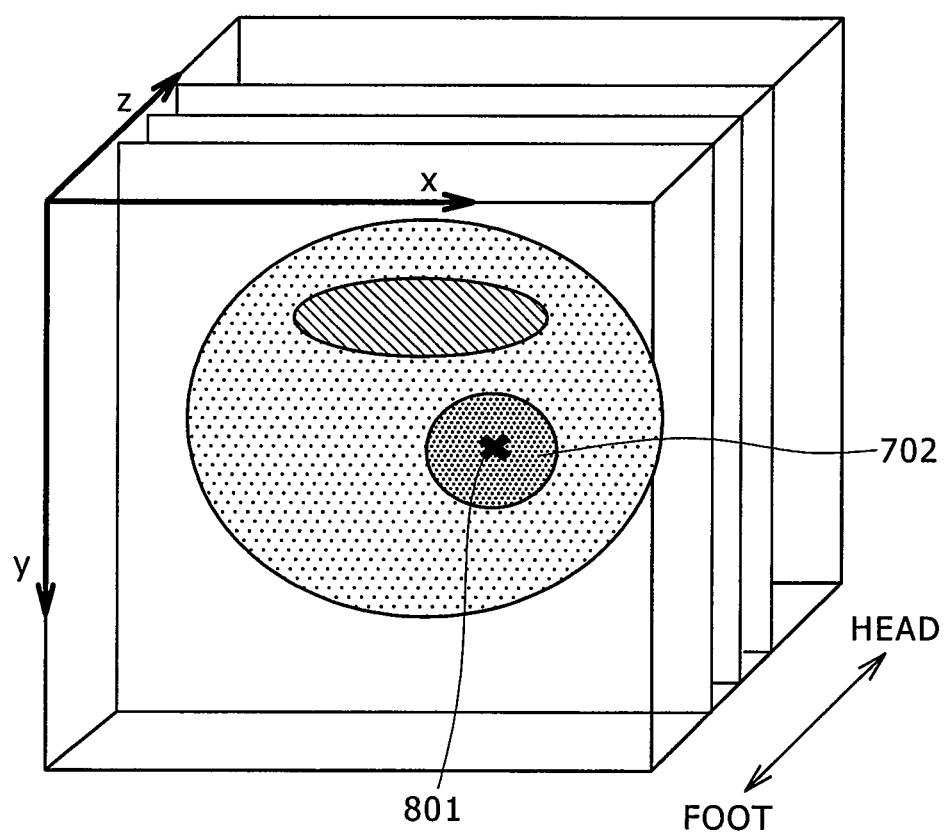
FIG. 14 is a diagram illustrating a coordinate system according to a second embodiment of the present invention.

The operator specifies the direction of target movement in a three-dimensional coordinate system, for example, like the one shown in FIG. 14, based on CT data. In FIG. 14, the foot-to-head direction is defined as z axis, and x and y axes are set to be perpendicular to the z axis, respectively. When the target is determined to move in the foot-to-head direction, the operator specify a three-dimensional direction in the coordinate system. For example, the operator inputs coordinate value (x, y, z)=(0, 0, 1) from an input screen like the one shown in FIG. 11.

When the direction of target movement is determined, the treatment planning system projects the direction specified in the coordinate system shown in FIG. 14 on the isocenter plane 804 and calculates the direction projected on the isocenter plane 804. When the direction on the isocenter plane 804 is determined, the operation of and subsequent to step 105 can be performed in the same way as in the first embodiment. Since the present embodiment requires no marker position to be determined for each phase, the operation to be performed by the operator is reduced.

According to the present embodiment, it is possible to input movement of a patient's affected area and generate treatment planning data to cause an ion beam to be scanned mainly in a direction coinciding with the direction of the movement, so that treatment planning data which can realize dose distribution with improved uniformity can be provided.

Third Embodiment

In the first and second embodiments, spots are arranged on straight lines parallel with a specified direction. In that way, when the specified direction is changed, the spot positions are also changed making it necessary to perform the operations beginning with step 203 shown in FIG. 2.

When a discrete scanning method in which ion beam irradiation is stopped during scanning is used, the dose distribution is not dependent on the scanning path as long as the spot positions remain unchanged. In this case, it is possible, unlike in the first and second embodiments, to change only the scanning path portion that begins at a predetermined spot into an arbitrary direction. Such a method will be described below as a third embodiment.

Figure 15:
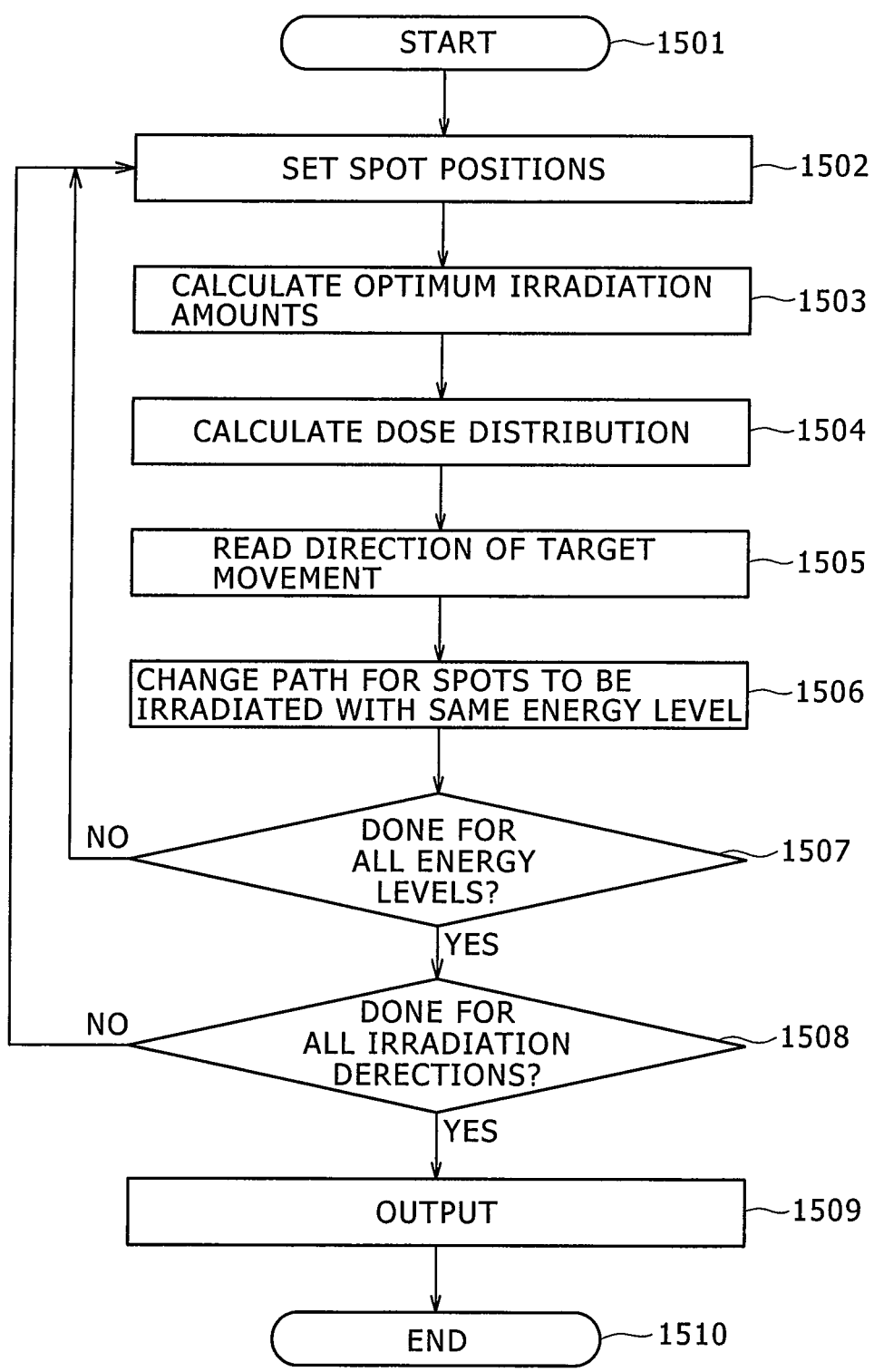
FIG. 15 is a flowchart for treatment planning by a treatment planning system according to a third embodiment of the present invention.

FIG. 15 shows the flow of operation, according to the third embodiment, corresponding to the automatic calculation performed by the treatment planning system 501 (step 105 shown in FIG. 1). After automatic calculation is started (step 1501), spot positions are selected (step 1502), the irradiation amount is optimized for each spot (step 1503), and dose distribution is calculated (step 1504) as done by an existing treatment planning system without taking the scanning direction into consideration.

In the method of the present embodiment, the scanning path is changed after dose distribution is calculated in step 1504. First, the direction of target movement specified in step 104 shown in FIG. 1 is read (step 1505). Subsequently, a scanning path is set as described below for spots to be irradiated with a same level of beam energy and from a same irradiation direction (step 506). When a scanning path is specified, the arithmetic processing unit 605 of the treatment planning system 501 prepares a function for converting the path into an appropriate value. For example, the function may be defined based on the total scanning distance along the scanning path such that its value is smaller when the scanning direction is closer to the direction specified in step 104. Out of various scanning paths, the one that makes the value of the defined function smallest is searched for, for example, using a simulated annealing algorithm, as an optimum scanning path.

Figure 16:
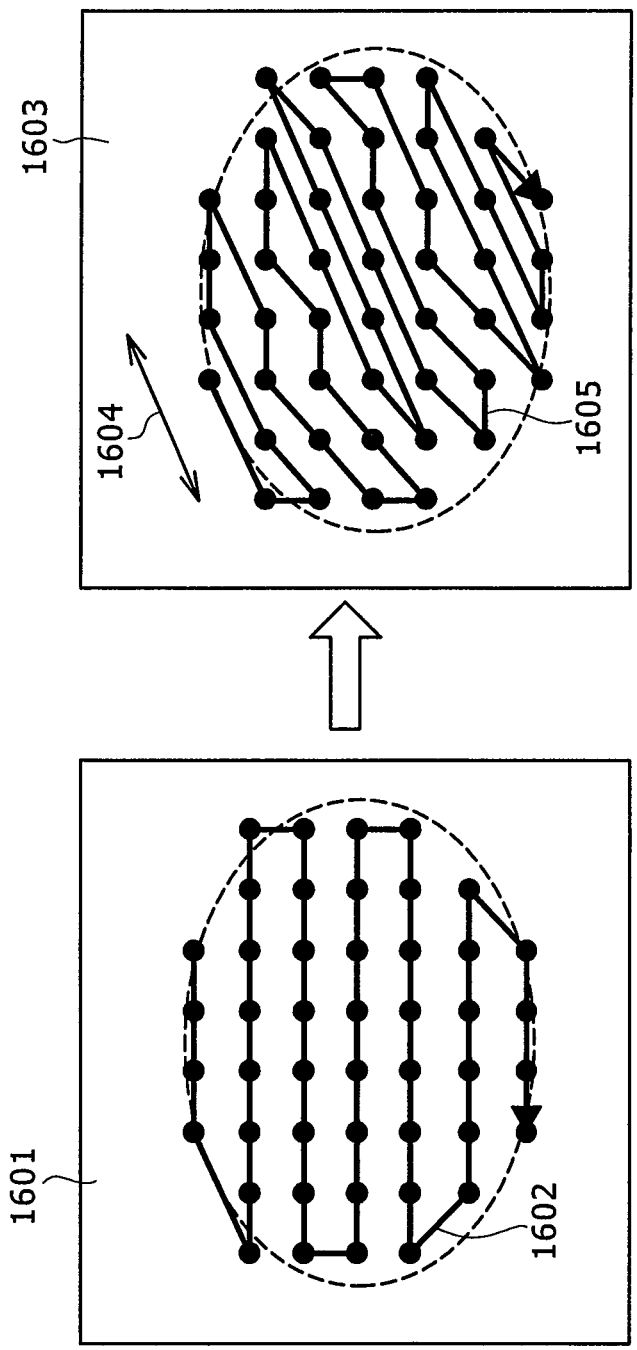
FIG. 16 is a conceptual diagram illustrating a scanning path change made by a method according to the third embodiment.

An example is shown in FIG. 16 in which reference numeral 1601 represents a state with an unchanged scanning path for spots to be irradiated with a same level of beam energy. Spot positions are represented by black circles and an arrow 1602 represents an initial scanning path. The scanning path 1602 has been set without taking into consideration the direction of target movement. Reference numeral 1603 represents a state with a scanning path changed based on a specified direction of target movement. The spot positions are not different between the two states. In the state 1603, however, a direction of target movement 1604 is specified and it is seen that a scanning path 1605 has been set to cause scanning to proceed mostly along the specified direction.

This is performed for every level of beam energy to be irradiated and every irradiation direction (determined by the angles of the gantry 311 and bed 407) (steps 1507 and 1508). Finally, the irradiation parameters including the scanning path information thus determined are outputted and the operation is ended (steps 1509 and 1510).

In the method of the present embodiment, the scanning path can be changed after the spot positions and the irradiation amount for each spot are determined. The scanning path can therefore be changed outside the treatment planning system. For example, there can be a case in which the scanning path is changed using the central control unit 312 immediately before ion beam irradiation. The treatment planning data generated by the treatment planning system 501 is stored in the data server 502. In performing ion beam irradiation, the data stored in the data server 502 is read by the central control unit 312. At that time, the central control unit can display the scanning path on the display device 315 and provide an interface for changing the scanning path, thereby allowing the operator to change the scanning path using an input device (not shown) provided for the central control device. By inputting instructions for changing the scanning path on a screen like the one shown in FIG. 11 or in a coordinate system like the one shown in FIG. 14, the operator can change the scanning path as done in step 1506.

According to the present embodiment, an ion beam scanning path can be changed by observing the state of a target immediately before starting ion beam irradiation, so that the movement of the target to be irradiated can be well reflected in treatment to be performed. Even though a scanning path can be changed immediately before starting ion beam irradiation by the methods of the first and second embodiments, too, the method of the present embodiment makes it possible to change only the scanning path without affecting the dose distribution. Thus, the present embodiment has advantages in that the scanning path can be changed requiring less time for calculation and in that advisability of the treatment plan after a change in the dose distribution can be checked (step 107) in a simple manner.

According to the present embodiment, it is possible to input movement of a patient's affected area and generate treatment planning data to cause an ion beam to be scanned mainly in a direction coinciding with the direction of the movement, so that treatment planning data which can realize dose distribution with improved uniformity can be provided.

What is claimed is:

1. A particle therapy system comprising:
    an ion beam accelerator;
    at least one device receiving direction information referring to target movement; and
    an irradiation control system controlling ion beam irradiation, a scanning direction of the ion beam irradiation being determined based on the received direction information referring to target movement.

2. A particle therapy system comprising:
    an ion beam accelerator;
    at least one device receiving, from an operator, direction information of ion beam irradiation; and
    an irradiation control system controlling the ion beam irradiation, the ion beam irradiation being scanned along the received direction information of ion beam irradiation.

3. The particle therapy system according to claim 1, wherein the ion beam irradiation is scanned along the received direction information projected on an isocenter plane.

4. The particle therapy system according to claim 1, wherein the direction information received by the at least one device being a direction of movement of a specific organ caused by respiration or heartbeat, wherein the irradiation control system scans the ion beam irradiation mainly in a direction coinciding with the received direction information of the organ movement.

5. The particle therapy system according to claim 1, further comprising a display device displaying a dose distribution calculated based on a certain spot position and a scanning path, the display device displaying an input screen enabling manually modifying the scanning direction of the ion beam irradiation.

6. The particle therapy system according to claim 1, further comprising a device enabling a modification of the ion beam irradiation direction, the modification making a component of the received direction perpendicular to an isoplane smaller.

7. The particle therapy system according to claim 2, wherein the ion beam irradiation is scanned along the received direction projected on an isocenter plane.

8. The particle therapy system according to claim 2, further comprising a display device displaying a dose distribution calculated based on a certain spot position and a scanning path, the display device displaying an input screen enabling manually modifying the scanning direction of the ion beam irradiation.

9. The particle therapy system according to claim 2, further comprising a device enabling a modification of the ion beam irradiation direction, the modification making a component of the received direction perpendicular to an isoplane smaller.

10. The particle therapy system according to claim 2, wherein the irradiation control system scans the ion beam irradiation mainly in a direction coinciding with the received direction information.

* * * * *